United States Patent
Zalevsky et al.

(10) Patent No.: US 9,199,081 B2
(45) Date of Patent: Dec. 1, 2015

(54) BLIND SIGHT

(75) Inventors: Zeev Zalevsky, Rosh Haayin (IL); Michael Belkin, Givat Shmuel (IL)

(73) Assignees: RAMOT AT TEL AVIV UNIVERSITY LTD. (IL); BAR-ILAN UNIVERSITY (IL)

(*) Notice: Subject to any disclaimer, the term of this patent is extended or adjusted under 35 U.S.C. 154(b) by 0 days.

(21) Appl. No.: 13/880,060

(22) PCT Filed: Oct. 17, 2011

(86) PCT No.: PCT/IB2011/054609
§ 371 (c)(1),
(2), (4) Date: Jun. 10, 2013

(87) PCT Pub. No.: WO2012/052912
PCT Pub. Date: Apr. 26, 2012

(65) Prior Publication Data
US 2013/0253608 A1    Sep. 26, 2013

Related U.S. Application Data

(60) Provisional application No. 61/344,828, filed on Oct. 19, 2010.

(51) Int. Cl.
*A61N 1/36* (2006.01)
(52) U.S. Cl.
CPC .......... *A61N 1/3605* (2013.01); *A61N 1/36046* (2013.01)
(58) Field of Classification Search
CPC ................. A61N 1/3605; A61N 1/36046
USPC ....................................... 607/53–54
See application file for complete search history.

(56) References Cited

U.S. PATENT DOCUMENTS

| 5,935,155 | A | 8/1999 | Humayun et al. |
| 2003/0139784 | A1* | 7/2003 | Morimoto et al. ............... 607/54 |
| 2007/0121120 | A1* | 5/2007 | Schachar ....................... 356/496 |
| 2009/0052049 | A1* | 2/2009 | Batchko et al. ............... 359/666 |
| 2009/0312817 | A1 | 12/2009 | Hogle |
| 2010/0036457 | A1* | 2/2010 | Sarpeshkar et al. ............ 607/53 |

FOREIGN PATENT DOCUMENTS

WO    2010097096    9/2010

OTHER PUBLICATIONS

PCT International Search Report PCT/IB2011/054609 dated Aug. 20, 2012.
European Office Action dated Feb. 13, 2014 for corresponding European Application No. 11815710.6.
Elizabeth Cunningham Perkins; Wearable computers on eyeballs a reality? Digital Journal; Nov. 24, 2011; (http://www.digitaljournal.com/article/314936).

* cited by examiner

*Primary Examiner* — Catherine Voorhees
(74) *Attorney, Agent, or Firm* — A.C. Entis-IP Ltd.

(57) ABSTRACT

A sensory substitution device (SSD) for providing a person with neural signals responsive to features of an environment, the SSD comprising: at least one camera that acquires an image of the environment; and at least one corneal neural stimulator that stimulates nerve endings in the cornea of an eye of the person to generate neural signals responsive to the image that propagate to the person's brain.

18 Claims, 4 Drawing Sheets

BLIND SIGHT

RELATED APPLICATIONS

The present application is a US National Phase of PCT Application No. PCT/IB2011/054609, filed on Oct. 17, 2011, which claims the benefit under 35 U.S.C. §119(e) of U.S. Provisional 61/344,828 filed on Oct. 19, 2010, the disclosures of which are incorporated herein by reference.

TECHNICAL FIELD

Embodiments of the invention relate to sensory substitution devices (SSDs) in which non-retinal stimulus is used to generate input to the brain of visually compromised people to substitute for damage or loss of retinal input.

BACKGROUND

A person's perception of the environment responsive to sensory signals received from a sense organs such as an eye, an ear, or the skin, appears to be a subjective impression that the person's brain constructs to organize and correlate the sensory signals and provide the person with a conscious model that operates to interface the person with the environment. The interface enables the person to observe, record, and direct, his or her responses to features of the environment that are represented by the sensory signals.

The way the brain uses sensory signals from a given sense organ to generate a perception, and an efficiency with which it does so, are at least partially functions of learning, and different parts of the brain exhibit substantial plasticity in learning to generate perceptions responsive to signals from different sensory organs. For example, the occipital cortex of the brain in healthy people is responsible for providing visual perceptions and spatial models of an environment responsive to light collected from the environment by the eyes. In blind people who have suffered or been born with damage to the eyes or the neural system that transports signals from the eyes to the occipital cortex, the occipital cortex does not receive signals from the eyes. However, functional magnetic resonance imaging (fMRI) shows that the occipital cortex in blind people is often adapted to process audio signals generated by the ears and tactile signals generated by the fingers. The occipital cortex, by way of example, is generally involved in processing tactile signals produced by the fingers of blind people when they touch Braille letters to provide perceptions of the letters and read.

Blind people also appear to use the occipital cortex to generate spatial models of environments responsive to tactile or audio signals that are reminiscent of spatial models supported by visual perceptions in people who have normal sight. The spatial models that the blind appear to generate responsive to non retinal signaling enable them to function and navigate their environments in a manner that implies that their models share traits that characterize the models of sighted people.

The plasticity of the brain in learning to process sensory signals has been demonstrated in the development and use of SSDs that are designed to provide blind people with audio or tactile sensory input that substitutes for retinal signaling that they do not have. For example, in an SSD technology referred to as "vOICe", images of an environment acquired by a video camera mounted in a pair of glasses worn by a blind person are encoded in auditory signals. The auditory signals are provided to the person by stereo speakers mounted in the glasses to aid the person in interacting with, and navigating in, the environment. Blind users of the glasses have reported and shown that the audio signals they receive from the SSD enable them to distinguish visual features, such as objects and patterns, of the environment.

Some tactile SSD technologies convert images from a glasses mounted camera to electrical signals on small electrodes arrayed in a tongue display unit (TDU) worn on the tongue. The electrical signals generated responsive to an image acquired by the camera stimulate tactile sensations on small regions of the tongue to generate an image, a "tongue image" on the tongue that represents the camera image. BrainPort® technologies of WICO Inc in Wisconsin USA reports developing a 3 cm×3 cm TDU having about 600 electrodes for generating tongue images. Blind people using the device appear to perceive the tongue images as low resolution images of their environment and are able to use the tongue images to distinguish such features as another person's fingers or to play tic-tac-toe on a large, (about 30 cm×30 cm) tic-tac-toe grid.

SUMMARY

An aspect of an embodiment of the invention relates to providing a high resolution SSD in which the cornea is stimulated to generate neural signals, hereinafter also referred to as "corneal neural signals" or "corneal signals", that substitute for retinal signals, which are non-existent or impaired in a vision compromised person. The corneal neural signals encode and provide the person's brain with a representation, hereinafter also referred to as a "corneal neural image", of an image of an environment in which the vision compromised person is present that would normally be represented by retinal signals produced by the retina of a person having healthy vision. Optionally, the image of the environment is processed in accordance with a compression algorithm to reduce an amount of data that is used to stimulate the cornea and provide the corneal neural image. Optionally, stimulation of the cornea is configured to time multiplex the corneal neural signals and improve spatial resolution of images that the corneal neural signals provide to the brain.

Hereinafter an SSD that operates by stimulating the cornea in accordance with an embodiment of the invention, may be referred to as a "corneal SSD", and a vision compromised person who may benefit from an SSD is referred to as a blind person, independent of a degree to which his or her vision is compromised.

In an embodiment of the invention, a corneal SSD comprises a camera that acquires an image of an environment in which a blind person is present, and a corneal neural stimulator comprising an array of electrodes, which electrodes are in contact, or in close proximity, with the outer, epithelial surface of the cornea of at least one of the person's eyes. In an embodiment of the invention the electrodes, hereinafter also referred to as "corneal electrodes", are comprised in or on a surface of a rigid or pliable support substrate, hereinafter referred to as a "contact substrate" that contacts the epithelial surface of the cornea.

A controller applies voltages to the corneal electrodes responsive to the camera image to electrify the corneal electrodes in a pattern that represents the camera image. The electrified corneal electrodes produce stimuli of nerve endings in small localized regions, of the cornea respectively adjacent the corneal electrodes to map the camera image onto the cornea. A stimulus of a localized region of the cornea produced by electrifying a corneal electrode may comprise a change in pressure, temperature, electric field and/or electric current generated on and/or in the localized region. The stimulated nerve endings generate corneal neural signals, responsive to the stimuli that encode the camera image mapped onto the cornea into a corneal neural image. The corneal neural signals, and thereby the corneal neural image, propagate to the brain along sensory nerve fibers to which the nerve endings are coupled.

Following practice and training using the corneal SSD, the person's brain is expected to use corneal neural images it receives from the corneal SSD to generate representations of environments imaged by the camera that enable the blind person to distinguish features of the environments In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation, and are not necessarily shown to scale.

DETAILED DESCRIPTION

In the following detailed description, features of a corneal SSD in accordance with an embodiment of the invention are illustrated and discussed with reference to FIG. 1. Features of corneal neural stimulators that may be used in practice of embodiments of the invention are discussed with reference to FIGS. 2A and 2B. A method of multiplexing corneal neural signals in a corneal SSD similar to that shown in FIG. 1 to provide a blind person with a corneal image characterized by enhanced spatial resolution is discussed with reference to FIG. 3.

Figure 1:
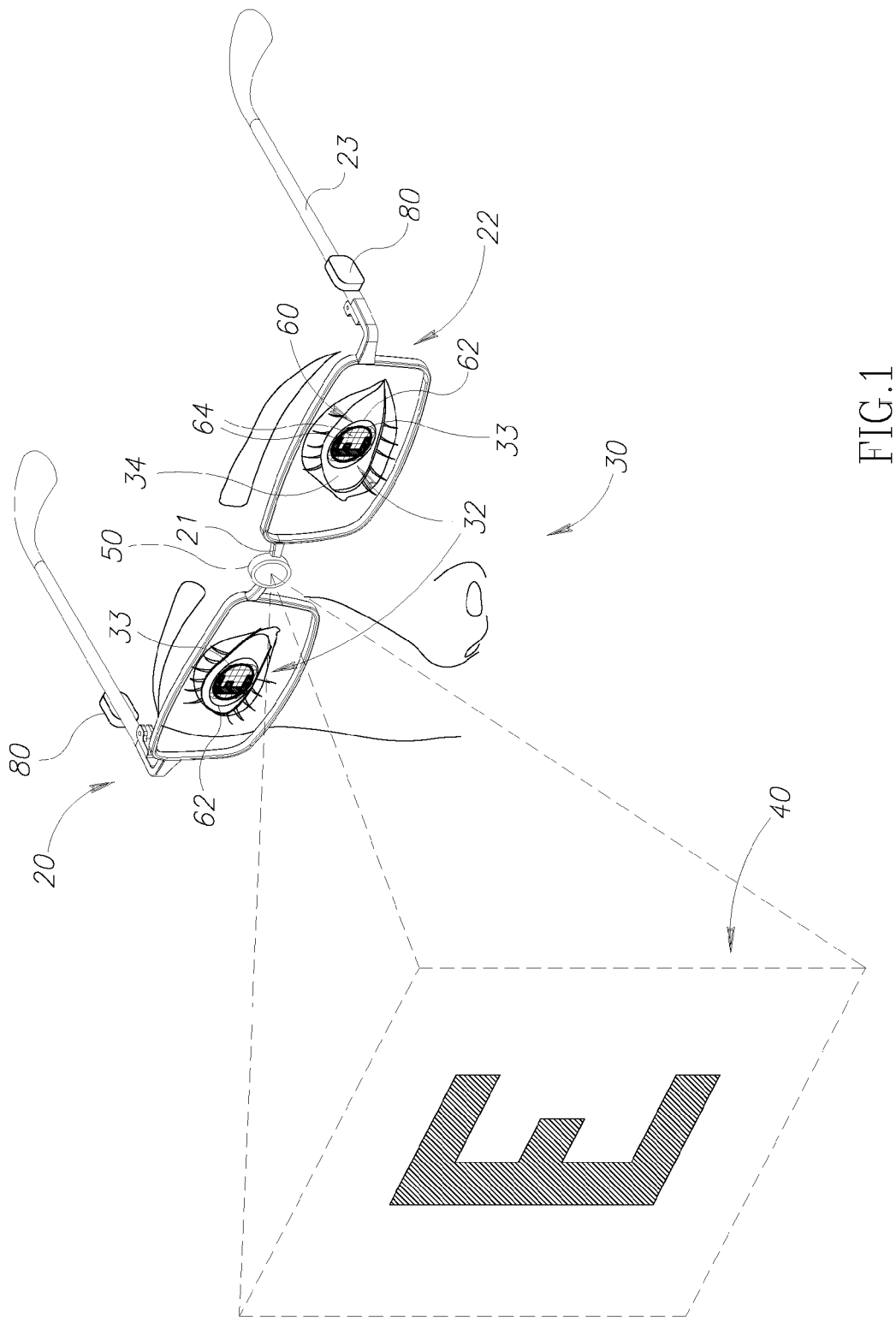
FIG. 1 schematically shows a blind person using a high resolution corneal SSD that stimulates the cornea to generate corneal neural signals responsive to his or her environment that substitute for retinal signals and aid the blind person to interact with the environment, in accordance with an embodiment of the invention.

FIG. 1 schematically shows a corneal SSD 20 in accordance with an embodiment of the invention being used by a blind person 30 to interact with an environment schematically indicated by a dashed rectangle 40. The environment is assumed to comprise objects represented by a letter "E".

Figure 2A:
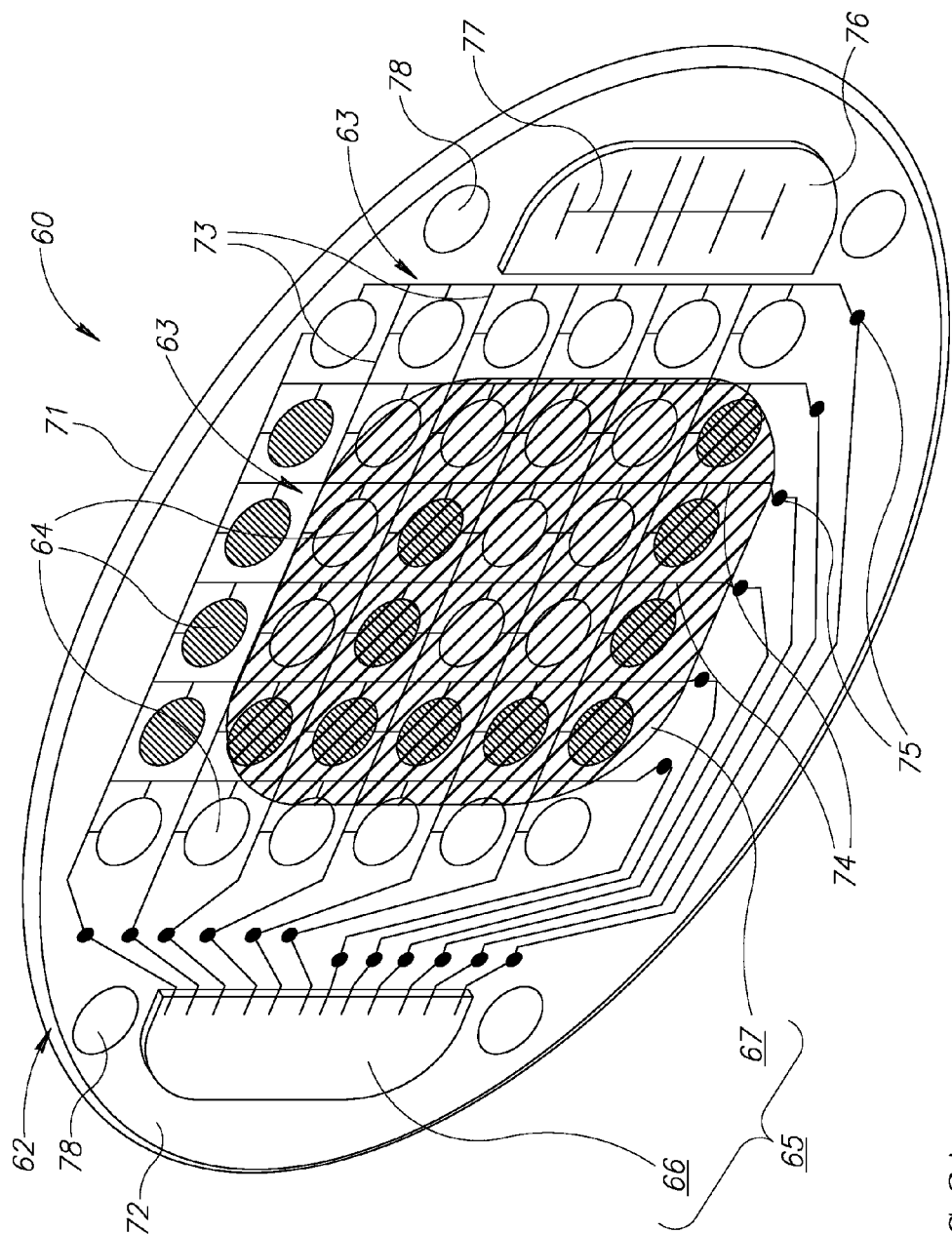
FIG. 2A schematically show a corneal neural stimulator comprised in the corneal SSD shown in FIG. 1 in accordance with embodiments of the invention.

Corneal SSD 20 optionally comprises a camera 50 that images environment 40, and a corneal neural stimulator 60, optionally for each eye 32 of blind person 30. Camera 50 may be mounted to any suitable support, such as a helmet, pair of glasses, or a chest harness, that may be worn by person 30. Optionally as shown in FIG. 1, camera 50 is mounted to a bridge 21 of a pair of glasses 22 worn by the blind person. Controllers 80, optionally mounted on side bars 23 of the glasses, control corneal neural stimulators 60 responsive to images of environment 40 acquired by camera 50. Features of the corneal neural stimulators that are too small to be conveniently shown in FIG. 1 are shown in FIG. 2A, which shows a greatly enlarged view of a corneal neural stimulator 60 and components that it comprises.

In an embodiment of the invention, corneal neural stimulator 60 comprises a contact substrate 62, having an array 63 of corneal electrodes 64 (FIG. 2A) that contact or are in close proximity to the cornea 33 of the eye and electrification circuitry 65 for electrifying the corneal electrodes. Contact substrate 62 may be formed as a relatively thin layer of a rigid or pliable material and has first and second surfaces 71 and 72 respectively. The first surface contacts the cornea of eye 32 and may also be referred to as corneal contact surface 71. The second surface may also be referred to as an external surface 72 of contact substrate 62.

In an embodiment of the invention contact substrate 62 is formed having a shape and curvature reminiscent of that of a contact lens, and is configured to match that of cornea 33 so that it may seat comfortably on the cornea. Any of various materials used to form rigid contact lenses, such as polymethyl methacrylate or an oxygen-permeable polymer may be used to form contact substrate 62 as a rigid substrate. Alternatively, contact substrate may be formed as a thin layer of a relatively pliable substrate from a material such as a polyimide, PEEK, or polyester.

Electrification circuitry 65 comprises an electrification controller 66 and a capacitor 67 that provides power for operating the electrification circuitry and electrifying corneal electrodes 64. In an embodiment of the invention components of circuitry comprised in contact substrate 62 are electrically grounded to the body of person 30. Optionally, grounding is provided by a contact electrode (not shown) that provides electrical contact of circuitry in corneal neural stimulator 60 with sclera 34 of eye 32 (FIG. 1). In an embodiment of the invention, the corneal electrodes are formed on or in contact substrate 62 and relatively close to corneal contact surface 71. Optionally, corneal electrodes 64 are formed on corneal contact surface 71.

Electrification controller 66 is optionally formed on external surface 72 of contact substrate 62 and is connected to corneal electrodes 64 by row and column control lines 73 and 74 respectively. Optionally, electrification controller 66 is electrically connected to each of the row and column control lines at connection nodes 75. Control lines 73 and 74 and/or contact nodes 75 may be formed on corneal contact surface 71, or external surface 72 of contact substrate 62 or in the substrate.

Electrification circuitry 65 applies voltage to a given corneal electrode 64 by transmitting appropriate signals along row and column control lines 73 and 74 that are connected to the given corneal electrode. Optionally, each corneal electrode 64 is connected to control lines 73 and 74 by a thin flat transistor (TFT) circuit (not shown) comprising at least one TFT transistor which operates to apply voltage to the electrode when the appropriate signals generated by electrification circuitry 65 are applied to control lines 73 and 74. Any of various technologies known in the art, such as ink jet printing, may be used to produce the TFT circuit. Optionally, the TFT circuit is similar to a TFT circuit controllable to apply voltage to pixels in a photosensor of a digital camera. Charge required to apply voltage to the given corneal electrode 64 is supplied by capacitor 67, which is charged to a predetermined supply voltage relative to the sclera of the eye.

In an embodiment of the invention, each controller 80 (FIG. 1) controls a corneal neural stimulator 60 to which it is closest to electrify corneal electrodes 64 in the corneal neural stimulator responsive to images of environment 40 acquired by camera 50 and to maintain capacitor 67 charged to the desired supply voltage. The controller is connected to camera 50 and the corneal neural stimulator 60 that it controls by any of various suitable physical or wireless communication channels. A physical communication channel may be supported by a conductive wire or an optic fiber. A wireless communication channel may be a logical channel mediated by RF or ultrasound signals. It is noted that whereas controllers 80 are shown and described as mounted to sidebars 23 of glasses 22, the controllers may of course be comprised in circuitry housed in camera 50 and/or circuitry comprised in corneal neural stimulators 60.

In FIG. 1 by way of example, controller 80 is connected to corneal neural stimulator 60 by an RF wireless channel and contact substrate 62 of the corneal neural stimulator comprises an RF front end 76 connected to an RF antenna 77 for receiving and processing control signals from controller 80. Optionally, controller 80 transmits power signals for charging capacitor 67 to RF front end 76, which are received by antenna 77. The RF front end extracts energy from the power signals and uses the extracted energy to maintain the capacitor charged to the desired supply voltage. The controller is assumed connected to camera 50 by a wire channel (not shown) mounted to or embedded in glasses 22.

Following acquisition of an image of environment 40 by camera 50 (FIG. 1) controller 80 receives image data from the camera that defines features in the image. The controller transmits control signals to corneal neural stimulator 60 for controlling electrification circuitry 65 responsive to the image data that are received by RF antenna 77 and processed by RF front end circuit 76. The processed signals are transmitted by RF front end 76 to electrification circuitry 65 to control the electrification circuitry to apply voltages to corneal electrodes 64 in array 63 so that a spatial configuration of electrified corneal electrodes 64 reproduces features in environment 40 imaged by camera 50.

In FIG. 1 by way of example, objects in the environment that are imaged by camera 50 are, as noted above, represented by the letter E, and corneal electrodes 64 that are electrified by voltage from electrification circuitry 65 are shown shaded in FIGS. 1 and 2A, and reproduce the letter E to indicate that the pattern of electrified electrodes reproduces the imaged objects.

The voltage on each electrified corneal electrode 64 produces an electric field, and optionally current, for example a leakage or an induced current, which stimulates nerve endings in a localized region of cornea 33 opposite the electrode to generate neural signals. The corneal neural signals stimulated by the electrified corneal electrodes 64 encode the camera image of environment 40 as a corneal neural image that is transmitted to the brain of blind person 30 and used by the brain to interface the blind person with environment 40.

Whereas corneal SSD 20 is shown comprising a single camera 50 and corneal neural stimulators 60 are indicated as generating same patterns of corneal neural stimulation to represent environment 40 on cornea 33 of both right and left eyes 32 of blind person 30 a corneal SSD in accordance with an embodiment of the invention is not limited to comprising a single camera and providing a same "stimulation image" to both eyes. For example, a corneal SSD in accordance with an embodiment of the invention may comprise two cameras (or a suitable stereo camera) that acquire images of an environment, such as environment 40, from different respective locations to provide a stereo pair of left and right images of the environment. The left and right images are used by left and right corneal neural stimulators 60 to stimulate cornea 33 of the left and right eyes 32 respectively of person 30 to generate corneal neural images of environment 40 that encode binocular disparity to aid the person's brain in generating a sense of depth for features in the environment.

It can be advantageous for corneal neural stimulator 60 to be stationary relative to cornea 33 of eye 32 (FIG. 1) on which it is positioned so that nerve endings in a same region of the cornea are stimulated responsive to an object in environment 40 that is stationary relative to the eyes of blind person 30. In an embodiment of the invention, to maintain corneal neural stimulator 60 substantially stationary relative to the cornea, contact substrate 62 comprises at least one, and optionally as shown in FIG. 2A four, stabilizing electrodes 78 (FIG. 2A). Each stabilizing electrode 78 is insulated from, optionally sclera 34, of eye 32 by a layer (not shown) of material having a relatively high dielectric constant. Stabilization is provided by maintaining a voltage difference between stabilizing electrodes 78 and the sclera. For the applied voltage, the layer of dielectric material between each stabilizing electrode 78 and the sclera results in production of a relatively large electric field between the sclera and the dielectric material that strongly attracts and holds the dielectric, and thereby the corneal neural stimulator 60 in place over the sclera.

Whereas in the above description, corneal electrodes 64 are described as stimulating nerve endings in cornea 33 by being controlled to generate electric fields and/or currents in localized regions of cornea 33, practice of embodiments of the invention is not limited to stimulating corneal nerve endings by subjecting the nerve endings to electric fields or currents. Nerve endings in an embodiment of the invention may be stimulated by a change in pressure and/or temperature generated by electrification of corneal electrodes 64.

For example, a microfluidic system actuated by electrodes in the stimulator may be used to move a fluid, such as a liquid or a gas, in micro channels formed in a corneal neural stimulator, to generate changes pressure on localized regions of cornea 33. Optionally, each micro channel is a blind channel capped by a resilient membrane. Fluid moved by the corneal neural stimulator along a micro channel may cause the resilient membrane to deform and assume a convex or concave geometry. In the convex geometry the membrane may push and increase pressure on a region of the cornea. In the concave geometry the membrane may pull away from the region to generate a partial vacuum that reduces pressure on the region.

Figure 2B:
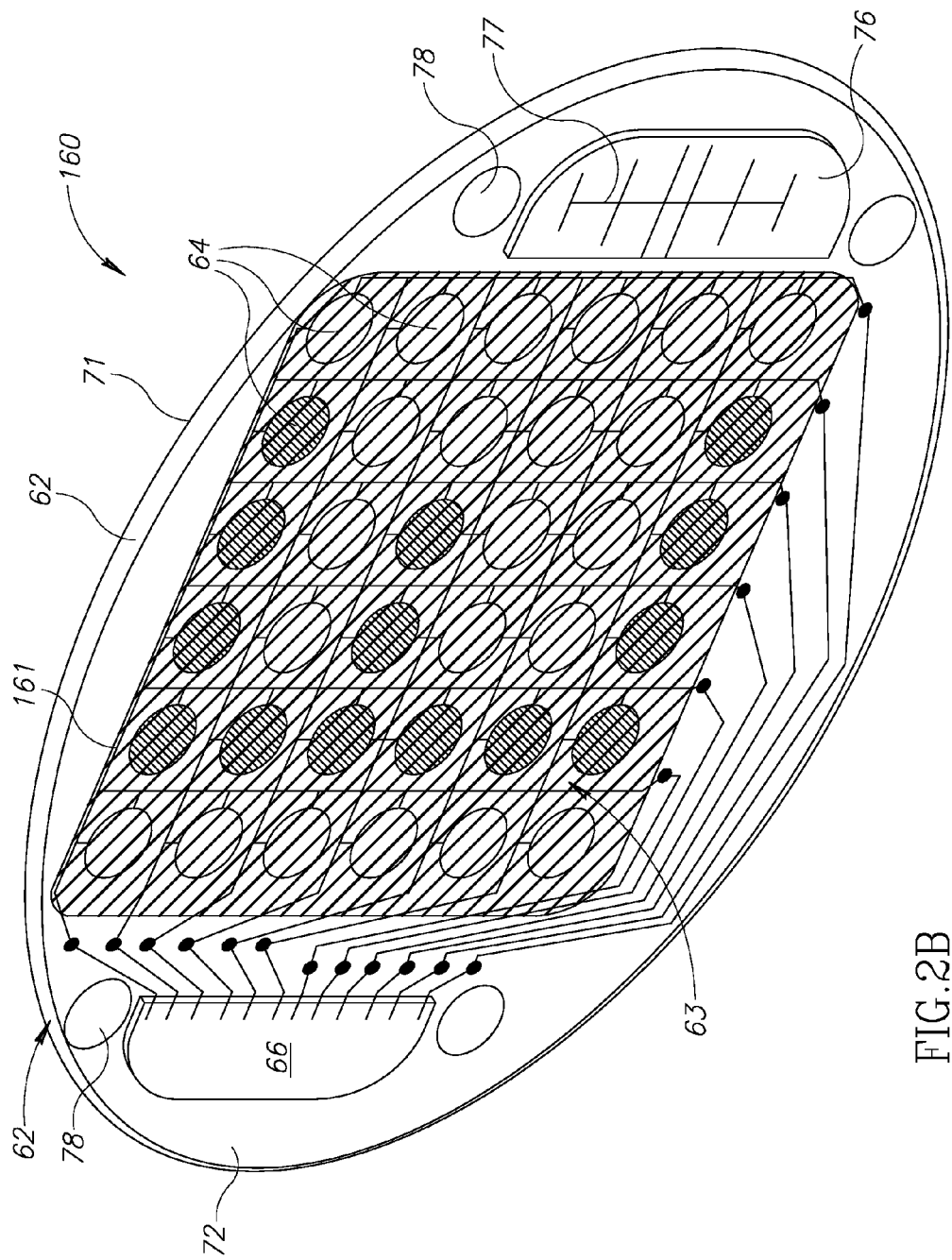
FIG. 2B schematically show another corneal neural stimulator, in accordance with embodiments of the invention.

By way of another example, FIG. 2B schematically shows a corneal neural stimulator 160 comprising a piezoelectric material in accordance with an embodiment of the invention that may be used in place of corneal neural stimulator 60. Neural stimulator is controllable to apply changes in pressure to small regions of cornea 33.

Corneal neural stimulator 160 optionally shares many of the features that are present in corneal neural stimulator 60, and comprises an optionally elliptical contact substrate 62, corneal electrodes 64, electrification controller 66, RF antenna 77, and RF front end 76. However, contact substrate 62 has a large electrode 161 opposite corneal electrodes 64 and material in the contact substrate sandwiched between the large electrode and the corneal electrodes is formed from a piezoelectric material.

In an embodiment of the invention all of contact substrate 62 is formed from a piezoelectric material. Optionally, the piezoelectric material between a corneal electrode 64 and large electrode 161 is comprised in an insert seated in a recess or hole (not shown) formed in the contact substrate. Optionally, the piezoelectric insert is large enough so that it is sandwiched between a plurality of corneal electrodes 64 and large electrode 161. Optionally, large electrode 161 and electrification circuitry 66 share a common ground. Various piezoelectric materials that may be used in corneal neural stimulator 60 include by way of example, a piezoelectric polymer such as Polyvinylidene fluoride (PVDF), and any of various ceramics such as Lead zirconate titanate (PZT-Pb[$Zr_x Ti_{1-x}$]$O_3$ $0 \leq x \leq 1$), lanthanum doped Lead zirconate titanate (PLZT), Barium titanate ($BaTiO_3$), or Sodium potassium niobate (NaKNb).

Optionally large electrode 161 functions as a first electrode of a capacitor (not shown) for storing energy for powering electrification circuitry, RF front end 76, and electrifying corneal electrodes 64. Optionally, the capacitor comprises a second electrode (not shown) on a side of large electrode 161 opposite the side of the large electrode in which corneal electrodes 64 are located.

Application of voltage by electrification controller 66 to a given corneal electrode 64 relative to large electrode 161 causes the piezoelectric material between the corneal electrode and the large electrode to contract or expand and generate thereby a change of pressure on a region of cornea 33 adjacent the given corneal electrode. The change in pressure stimulates nerve endings in the region adjacent the given corneal electrode to generate neural signals.

By way of a numerical example, in an embodiment of the invention, contact substrate 62 comprised in corneal neural stimulator 60 is elliptical in shape having minor and major axes greater than a diameter of cornea 33. An average diameter for a cornea is about 1.15 cm. Optionally, the minor and major axes (respectively perpendicular and parallel to the ground when blind person 30 is standing) of the ellipse are equal to or greater than about 1.2 cm. Optionally, the major axis is greater than or equal to about 2 cm. In an embodiment of the invention, thickness of contact substrate 62 is between about 0.08 mm (millimeters) and about 0.2 mm.

In an embodiment of the invention corneal neural stimulator 60 or 160 (FIGS. 2A, 2B) comprises at least 100 corneal electrodes 64. Optionally, the corneal neural stimulator comprises at least 500 corneal electrodes 64. Optionally, the corneal neural stimulator comprises at least 1000 corneal electrodes 64. In an embodiment of the invention, the corneal neural stimulator comprises at least 4,000 corneal electrodes. However, whereas there are about 60,000 nerve endings in the cornea that can be stimulated by electrification of corneal electrodes 64, the nerve endings branch off from only about 4,000 nerve fibers or nerve fiber bundles, hereinafter referred to as nerve fibers. Each nerve fiber therefore transmits neural signals to the brain from about 15 corneal nerve endings and the nervous system appears to be able to support simultaneous transmission of a maximum of about 4,000 signals generated by stimulation of nerve endings in the cornea.

Assume that the nerve endings are substantially evenly distributed over the area of the cornea. Assume further that nerve endings that branch from a same nerve fiber are clustered together in a same small surface region of the cornea and that nerve endings that branch from different nerve fibers are clustered in different surface regions of the cornea. Under these assumptions, an advantageous configuration of corneal electrodes 64 in array 63 (FIG. 2A) in accordance with an embodiment of the invention comprises about 4,000 corneal electrodes. Optionally, array 63 is a square array that substantially covers cornea 33 and in which the corneal electrodes are substantially evenly distributed with a pitch equal to about 0.16 mm. The number and distribution of corneal electrodes in the advantageous configuration enables stimulating the maximum number of independent neural signals that can substantially simultaneously be propagated to the brain by the nervous system from nerve endings in the cornea. Because of limitation of the nervous system, a number of corneal electrodes 64 greater than about 4,000 may not enable simultaneous transmission of more information to the brain than that simultaneously enabled by the about 4,000 electrodes.

Were all of an image of environment 40 acquired by camera 50 in corneal SSD 20 simultaneously mapped to cornea 33 by electrification of 4,000 corneal electrodes 64, visual information in the camera image would be encoded, and transported to the brain, in a corneal neural image comprising only about 4,000 corneal neural signals. The corneal neural image would therefore have a spatial resolution similar to that provided by camera 50 were the camera to image environment 40 on a photosensor in the camera having about 4,000 pixels. Whereas a spatial resolution equivalent to about 4,000 pixels for a corneal neural image in accordance with an embodiment of the invention is far greater than that provided by TDU images or audio images provided by conventional SSDs, it is substantially below a resolution of an image provided by a healthy human retina which comprises about $1.2 \times 10^6$ pixels.

Figure 3:
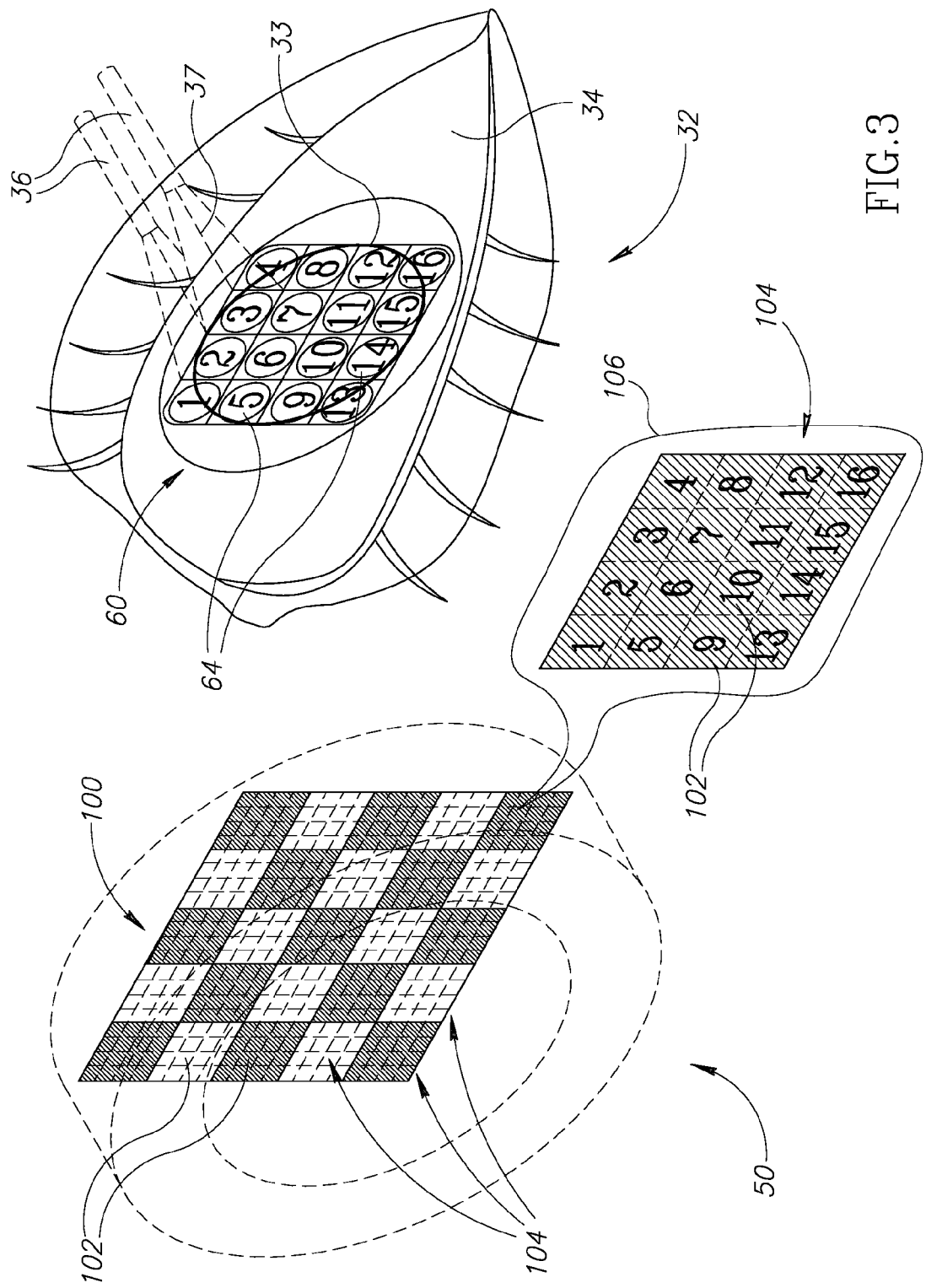
FIG. 3 schematically illustrates a method for configuring stimulus of the cornea to time multiplex corneal neural signals and provide the blind person with a corneal neural image characterized by enhanced spatial resolution in accordance with an embodiment of the invention.

To provide a corneal image having resolution greater than that supported by about 4,000 simultaneously stimulated nerve endings, in accordance with an embodiment of the invention, corneal SSD 20 stimulates nerve endings in the cornea to time multiplex data defining images acquired by camera 50 of an environment, such as environment 40, in which blind person 30 may be present. FIG. 3 graphically illustrates a method of time multiplexing images provided by camera 50 to provide blind person 30 with corneal neural images characterized by enhanced spatial resolution in accordance with an embodiment of the invention.

FIG. 3 schematically shows greatly enlarged images of camera 50 and corneal neural stimulator 60, which are comprised in SSD 20 and shown in FIG. 1. Corneal neural stimulator 60 is contiguous with cornea 33 of an eye 32 of blind person 30 FIG. 1. Camera 50 is shown in dashed lines to indicate that a photosensor 100 on which the camera images environments of blind person 30 is an internal component of the camera shown as if the camera were transparent. Photosensor 100 is assumed to comprise a number "NP" of light sensitive pixels 102. NP is arbitrarily shown equal to 400 in FIG. 3 and the pixels are shown configured in a square array of 20 rows and 20 columns of pixels.

For convenience of presentation, in FIG. 3 cornea 33 is assumed to be a "simplified cornea" innervated with nerve endings that branch off from a number "NF" of nerve fibers arbitrarily shown equal to sixteen rather than equal to the about 4,000 nerve fibers that actually innervate a real human cornea. Corneal neural stimulator 60 is schematically shown comprising a "matching number" of sixteen corneal electrodes 64. Corneal electrodes 64 are individualized by numeral labels 1-16. Each corneal electrode 64 is assumed to overlay a plurality of nerve endings (not shown) in cornea 33 that generate corneal neural signals which are propagated from the nerve endings to the brain of the blind person by a same neural fiber of the sixteen neural fibers that innervate the cornea.

In FIG. 3 nerve fibers for nerve endings in regions of cornea 33 underlying corneal electrodes 64 numbered 2 and 3 respectively are schematically indicated by dashed rods 36. A cone 37 in dashed lines extending from each nerve fiber 36 schematically connects the nerve fiber to a region of cornea 33 from which the nerve fiber receives corneal neural signals produced by nerve endings in the region when they are stimulated by electrification of corneal electrode 64 overlying the region.

Were all of an image of environment 40 acquired by camera 50 transferred to the brain of blind person 30 (FIG. 1) by stimulation of simplified (sixteen nerve fibers) cornea 33, the transferred image would be limited to about sixteen pixels and would be characterized by a corresponding relatively low spatial resolution. However, camera 50 as noted above acquires images of environment 40 on photosensor 100 having four hundred pixels, which images are therefore characterized by a spatial resolution substantially better than that supported by sixteen nerve fibers.

To preserve the spatial resolution provided by an image acquired by camera 50, in accordance with an embodiment of the invention, SSD 20 segments the image into "NI" partial images. Each partial image corresponds to a portion of the complete image that is provided by a number of optionally contiguous pixels 102 in photo sensor 100 equal to the number NF of nerve fibers 36. The number NI of partial images is therefore equal to NP/NF.

By way of example, for the number NP=400 of pixels 102 shown for photosensor 100 in FIG. 3 and NF=16, SSD 20 segments an image of environment 40 (FIG. 1) imaged by camera 50 on the photosensor into NI=25 partial images, each partial image provided by an optionally square group 104 of sixteen contiguous pixels 102. Groups 104 of pixels 102 that provide the partial images are alternately shown shaded and unshaded in photosensor 100 for ease of viewing.

The complete image of environment 40 is time multiplexed to the brain of blind person 30 by sequentially mapping the partial images onto cornea 33 so that the partial images are transmitted to the brain in a time series of corresponding "partial", corneal neural images. A partial image is mapped onto cornea 33 by electrifying each corneal electrode 64 responsive to an amount of light registered by a homologous pixel in the group 104 of pixels 102 on which camera 50 imaged the partial image. Optionally, electrifying a corneal electrode 64 responsive to an amount of light registered by a homologous pixel 102 comprises applying a voltage to the corneal electrode that increases with an increasing amount of light registered by the pixel. In FIG. 3 a group 104 of pixels 102 being mapped onto cornea 33 is shown greatly enlarged in an inset 106. Pixels 102 in the group are individualized by the numeral labels 1-16 that individualize corneal electrodes 64, and corresponding homologous pixels 102 and corneal electrodes 64 are labeled with a same numeral.

The complete corneal neural image of the environment comprising all the partial corneal neural images mapped to the cornea and time multiplexed to the brain comprises information defining NI×NF=NP pixels, which is equal to the number of pixels in the image of environment 40 acquired by camera 50. The complete image multiplexed to the brain therefore is characterized by an enhanced spatial resolution supported by NP pixels, which is about NI times that provided by information defining pixels simultaneously transmitted by NF nerve fibers.

For a real cornea innervated with nerve endings branching from about NF=4,000 nerve fibers and a corneal neural stimulator comprising about 4,000 corneal electrodes 64, an SSD in accordance with an embodiment of the invention segments an image acquired by camera 50 into NI partial images each defined by 4,000 pixels. The SSD therefore provides a blind person with a multiplexed corneal neural image having a spatial resolution similar to that of about NI×4,000 pixels. In an embodiment of the invention, NI is equal to or greater than about 50 to provide a corneal neural image having a spatial resolution equal to or greater than about 200,000 pixels. Optionally, NI is equal to or greater than about 100 to provide a corneal neural image having a resolution at least equal to about 400,000 pixels.

In some embodiments of the invention an image of an environment acquired by camera 50 is compressed prior to being used to generate corneal neural images. Any of various image compression algorithms, such as algorithms based on Fourier, cosine, sine or Hadamard transforms, may be used to compress an image acquired by the camera.

In an embodiment of the invention, an image of an environment acquired by camera 50 is compressed by processing the image using a pattern recognition algorithm to identify features and/or objects that appear relatively frequently in environments imaged by the camera. Each of the features or objects is associated with an ID code that identifies the feature or object. Whereas an amount of data comprised in pixels 102 (FIG. 3) imaging the feature or object in a given image of the environment can be very large, an amount of data defining the ID code identifying the feature or object is relatively short. In accordance with an embodiment of the invention, a corneal neural stimulator 60 is controlled to map the code identifying a feature or object in an image of an environment acquired by camera 50 rather than pixels 102 on which the feature and/or object is imaged by the camera onto cornea 33 of an eye. By mapping the code of the feature or object rather than the pixels onto the corneal substantially less data is required to be transmitted to the brain in a corneal neural image to define the feature or object.

It is noted that whereas in the figures and above discussion of a corneal neural stimulator in accordance with an embodiment of the invention the stimulator is described as stimulating nerve endings in the cornea. In some embodiments of the invention, a corneal neural stimulator may also stimulate nerve endings in the sclera. For example, array 63 of electrodes 64 in a corneal neural stimulator 60 (FIG. 1, FIG. 3) may extend beyond cornea 33 of the eye of blind person 30 on which it seats so that some of the electrodes in the array lie over sclera 34 of the eye. The electrodes overlying regions of the sclera may be used to stimulate nerve endings in localized regions of the sclera.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to person's of the art. The scope of the invention is limited only by the claims.

The invention claimed is:

1. A sensory substitution device (SSD) for providing a person with neural signals responsive to features of an environment, the SSD comprising:
   at least one camera that acquires an image of the environment; and
   at least one corneal neural stimulator comprising a substrate, the substrate being configured to seat on the cornea of a person's eye and having a plurality of electrodes that are electrifiable to stimulate nerve endings in different localized regions of the cornea to generate neural signals representing the image that propagate to the person's brain along nerve fibers from which the nerve endings branch.

2. An SSD according to claim 1 wherein the at least one corneal neural stimulator comprises a corneal neural stimulator to stimulate nerve ending in the cornea of a left eye and a corneal stimulator to stimulate nerve endings in the cornea of a right eye.

3. An SSD according to claim 2 wherein the at least one camera acquires images of the environment from different locations to provide a stereo pair of left and right images of the environment.

4. An SSD according to claim 1 wherein the plurality of electrodes equal to or greater than about 100.

5. An SSD according to claim 1 wherein the plurality of electrodes comprises a number of electrodes equal to about a number of nerve fibers in the cornea from which the nerve endings branch off.

6. An SSD according to claim 1 wherein the stimulus comprises a change in pressure in at least one of the different localized regions.

7. An SSD according to claim 1 and further comprising a controller configured to electrify the electrodes to sequentially stimulate nerve endings in the cornea responsive to different portions of the image so that the nerve fibers propagate time multiplexed neural signals representing the image to the brain.

8. An SSD according to claim 7 wherein the controller processes the image to provide a compressed image.

9. An SSD according to claim 8 wherein to provide the compressed image the controller replaces a portion of the image in which a feature or object in the environment is imaged with a code that identifies the imaged feature or object.

10. A method for providing a person with neural signals responsive to features of an environment, the method comprising:
    acquiring an image of the environment; and
    stimulating nerve endings in different localized regions of the cornea of at least one eye of the person to generate neural signals representing the image that propagate to the person's brain along nerve fibers from which the nerve endings branch.

11. A method according to claim 10 wherein acquiring an image comprises acquiring a stereo pair of right and left images of the environment.

12. A method according to claim 10 wherein stimulating nerve endings comprises stimulating the nerve endings to generate a sequence of time multiplexed neural signals.

13. A method according to claim 10 wherein stimulating nerve endings comprises processing the image of the environment to provide a compressed image and stimulating the nerve endings responsive to the compressed image.

14. A method according to claim 10 wherein stimulating the nerve endings comprises generating a change in a localized region of the cornea, the change comprising at least one change or any combination of changes chosen from the group consisting of: a change in electric field; a change in a current; a change in temperature; and a change in pressure.

15. An SSD according to claim 1 wherein the stimulus comprises a change in electric field in the localized region.

16. An SSD according to claim 1 wherein the stimulus comprises a change in current in the localized region.

17. An SSD according to claim 1 wherein the stimulus comprises a change in temperature.

18. An SSD according to claim 6 wherein the substrate comprises a piezoelectric material and electrification of at least one of the plurality of electrodes generates contraction or extension in the piezoelectric material that causes a change in pressure to generate the stimulus.

* * * * *